(12) United States Patent
Harrison

(10) Patent No.: US 9,071,209 B1
(45) Date of Patent: Jun. 30, 2015

(54) SYSTEMS AND METHODS FOR A CURRENT SENSING PATCH-CLAMP AMPLIFIER

(71) Applicant: Intan Technologies, LLC, Los Angeles, CA (US)

(72) Inventor: Reid R. Harrison, Los Angeles, CA (US)

(73) Assignee: Intan Technologies, LLC, Los Angeles, CA (US)

( * ) Notice: Subject to any disclaimer, the term of this patent is extended or adjusted under 35 U.S.C. 154(b) by 111 days.

(21) Appl. No.: 13/952,510

(22) Filed: Jul. 26, 2013

(51) Int. Cl.
*H03F 3/45* (2006.01)

(52) U.S. Cl.
CPC .................................. *H03F 3/45071* (2013.01)

(58) Field of Classification Search
CPC ......................................................... H03F 3/45
USPC .................................... 330/260, 261, 259, 85
See application file for complete search history.

(56) References Cited

U.S. PATENT DOCUMENTS

| | | | | |
|---|---|---|---|---|
| 3,707,684 | A | * | 12/1972 | Nowell .............................. 330/9 |
| 5,559,470 | A | * | 9/1996 | Laber et al. ..................... 330/252 |
| 5,880,610 | A | * | 3/1999 | Nishizono et al. ............. 327/103 |
| 7,518,406 | B2 | * | 4/2009 | Isobe ............................... 326/83 |
| 7,560,988 | B2 | * | 7/2009 | Weng et al. .................... 330/260 |

OTHER PUBLICATIONS

Hamill, O. P. et al., "Improved patch-clamp techniques for high-resolution current recording from cells and cell-free membrane patches", Pflugers Archiv, 391, 1981, pp. 85-100.

Kodandaramaiah, Suhasa B. et al., "Automated whole-cell patch-clamp electrophysiology of neuron in vivo", Nature Methods, vol. 9, No. 6, Jun. 2012, pp. 585-587.
Neher, E. et al., "Single-channel current recorded from membrane of denervated frog muscle fibres", Nature, vol. 260, Apr. 1976, pp. 799-802.
Robinson, Donita , "Detecting subsecond dopamine release with fast-scan cyclic voltammetry in vivo", Clinical Chemistry vol. 49, No. 10, 2003, pp. 1763-1773.
Sakmann, Bert et al., "Single-Channel Recording", Springer, 2nd ed.; New York, NY, 2009, 705 pgs.
Sigworth, F. J. , "Design of the EPC-9, a computer-controlled patch-clamp amplifier. 1. Hardware", Journal of Neuroscience Methods, 56, 1995, pp. 195-202.
Tuthill, Mike , "A switched-current, switched-capacitor temperature sensor in 0.6-μm CMOS", IEEE Journal of Solid-State Circuits, vol. 33, No. 7, Jul. 1998, pp. 1117-1122.

(Continued)

*Primary Examiner* — Henry Choe
(74) *Attorney, Agent, or Firm* — Kwan & Olynick LLP

(57) ABSTRACT

Disclosed are systems, apparatus, and methods for sensing currents conducted via an electrode. In various embodiments, an apparatus may include an operational amplifier including a first input terminal, a second input terminal, and an output terminal. The first input terminal may be configured to electrically couple with the electrode. The apparatus may further include a feedback circuit coupling the output terminal of the operational amplifier to the first input terminal. The feedback circuit may comprise a plurality of transistor devices configured to generate a feedback current based on a voltage value of the output terminal. The plurality of transistors may be further configured to provide the feedback current to the first input terminal. The apparatus may also include a voltage source coupled to the second input terminal and configured to maintain a substantially constant voltage at the second input terminal.

20 Claims, 8 Drawing Sheets

(56) References Cited

OTHER PUBLICATIONS

Vittoz, Eric et al., "CMOS Analog Integrated Circuits Based on Weak Inversion Operation", IEEE, Journal of Solid-State Circuits, vol. SC-12, No. 3, Jun. 1977, pp. 224-231.

Weerakoon, Pujitha et al., "Patch-clamp amplifiers on a chip", Journal of Neuroscience Methods, vol. 192, No. 2, Oct. 2010, pp. 187-192.

* cited by examiner

SYSTEMS AND METHODS FOR A CURRENT SENSING PATCH-CLAMP AMPLIFIER

FIELD OF THE INVENTION

One or more embodiments relate generally to circuits, hardware, computer systems and software, and, more particularly, to patch-clamp amplifiers.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

In biological cells, ion channels or ion transporters/pumps may be used to maintain an electric potential across a cellular membrane, and/or to conduct an ionic current when the cell is depolarized. Patch-clamp techniques may be used to study the behavior of a single or multiple ion channels in a cellular membrane of a biological cell. An electrode may be coupled to the cellular membrane. Conventional patch clamp techniques may utilize glass micropipettes and analog electronics to monitor ion channel currents generated by the cellular membrane of the biological cell coupled to the electrode. The micropipette may be filled with a conductive solution, and a metal wire may be inserted to conduct an electrical current. The wire may be coupled to a patch-clamp amplifier and used to hold the voltage of the electrode and cellular membrane at a constant voltage value.

BRIEF SUMMARY

The following section presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In some embodiments, an apparatus is disclosed for sensing currents conducted via an electrode. The apparatus may comprise an operational amplifier including a first input terminal, a second input terminal, and an output terminal. The first input terminal may be configured to electrically couple with the electrode. The apparatus may further comprise a feedback circuit coupling the output terminal of the operational amplifier to the first input terminal, where the feedback circuit comprises a plurality of transistor devices that are configured to generate a feedback current based on a voltage value of the output terminal, and are further configured to provide the feedback current to the first input terminal. The apparatus may also include a voltage source coupled to the second input terminal and configured to maintain a substantially constant voltage at the second input terminal.

In various embodiments, the apparatus further comprises a first calibration circuit that includes a first current source configured to generate a first current in response to receiving a first input from a digital controller. The apparatus may further comprise a second current source configured to generate a second current in response to receiving a second input from the digital controller. The operational amplifier may be configured to generate a first output voltage in response to receiving the first current and may be further configured to generate a second output voltage in response to receiving the second current. The digital controller may be configured to determine one or more constants associated with the plurality of transistor devices based, at least in part, on the first output voltage and the second output voltage. At least one of the first current source or the second current source may be configured to provide a direct current (DC) offset to the first input terminal in response to the voltage value of the output terminal changing polarity.

In some embodiments, the apparatus may further comprise a second calibration circuit that includes a first resistive device coupled to a circuit ground, a first switch coupling the first input terminal to the first resistive device and having a first open position and a first closed position, where the first switch in the first closed position is configured to generate a first current. The apparatus may also include a second resistive device coupled to the circuit ground, and a second switch coupling the first input terminal to the second resistive device and having a second open position and a second closed position, where the second switch in the second closed position is configured to generate a second current. The apparatus may also include a thermal sensor configured to sense one or more thermal metrics associated with the plurality of transistor devices, and further configured to generate an output signal identifying the one or more thermal metrics. The apparatus may further include a digital controller configured to perform one or more calibration operations in response to the thermal sensor generating the output signal.

According to various embodiments, the plurality of transistor devices is arranged as a first set of transistor devices and a second set of transistor devices. The first set of transistor devices may include a first transistor device having a first controlling terminal coupled to the output terminal of the operational amplifier. The first transistor device may be configured to generate a first feedback current that is an exponential function of the voltage value of the output terminal. The first set of transistor devices may be configured to generate a positive feedback current by mirroring the first feedback current, and may be further configured to provide the positive feedback current to the first input terminal of the operational amplifier. The second set of transistor devices may include a second transistor device having a second controlling terminal coupled to the output terminal of the operational amplifier. The second transistor device may be configured to generate a second feedback current that is an exponential function of the voltage value of the output terminal. The second set of transistor devices may be configured to generate a negative feedback current by mirroring the second feedback current, and may be further configured to provide the negative feedback current to the first input terminal of the operational amplifier. In various embodiments, a first source terminal of the first transistor device may be coupled to a circuit ground, and a second source terminal of the second transistor device may be coupled to the circuit ground.

In various embodiments, a method is disclosed, where the method comprises: coupling a first input terminal of an operational amplifier to an electrode; setting a value of a voltage provided to a second input terminal of the operational amplifier; generating, using a plurality of transistor devices, a feedback current and providing the feedback current to the first input terminal and the electrode, the feedback current maintaining a substantially constant voltage at the first input terminal and the electrode; measuring a voltage at an output terminal of the operational amplifier; performing, using a computer system, one or more processing operations on the measured voltage; and determining a current flowing through the electrode during the measuring step based on a result of the one or more processing operations.

The method may further comprise performing one or more calibration operations, the one or more calibration operations comprising: generating a first current; measuring a first voltage at the output terminal of the operational amplifier; generating a second current; measuring a second voltage at the output terminal of the operational amplifier; and determining, using the computer system, one or more constants associated with the plurality of transistor devices based on the measured first voltage and second voltage. The one or more calibration operations may be performed in response to detecting one or more thermal conditions associated with the plurality of transistor devices. The first current may be generated by a first current source in response to receiving a first input from a digital controller, and the second current may be generated by a second current source in response to receiving a second input from a digital controller.

In various embodiments, the method may also comprise generating a direct current (DC) offset, where the DC offset is provided to the first input terminal in response to a voltage value of the output terminal changing polarity, and where the DC offset is generated by at least one of the first current source and the second current source. The method may further comprise repeating the measuring, performing, and determining steps to generate a plurality of data points. The method may also comprise coupling the electrode to a cellular membrane, where the coupling generates a seal between the electrode and the biological cell membrane.

According to various embodiments, a system is disclosed, where the system comprises a patch-clamp amplifier implemented on a chip. The patch-clamp amplifier may comprise: an operational amplifier including a first input terminal, a second input terminal, and an output terminal, the first input terminal being configured to electrically couple with an electrode; a feedback circuit coupling the output terminal of the operational amplifier to the first input terminal, the feedback circuit comprising a plurality of transistor devices configured to generate a feedback current based on a voltage value of the output terminal, and further configured to provide the feedback current to the first input terminal; a voltage source coupled to the second input terminal and configured to maintain a substantially constant voltage at the second input terminal. The system may also comprise an analog-to-digital converter coupled to an output port of the patch-clamp amplifier, where the analog-to-digital converter is configured to digitize an output generated by the patch-clamp amplifier. The system may also comprise a digital controller coupled to the analog-to-digital converter, where the digital controller is configured to determine a current at the first input terminal based on the digitized output received from the analog-to-digital converter. In various embodiments, the patch-clamp amplifier, the analog-to-digital converter, and the digital controller are implemented on a single microchip.

These and other features of the present invention will be presented in more detail in the following specification of certain embodiments of the invention and the accompanying figures which illustrate by way of example the principles of the invention.

BRIEF DESCRIPTION OF THE DRAWINGS

In the following drawings like reference numbers are used to refer to like elements. Although the following figures depict various examples, the one or more embodiments are not limited to the examples depicted in the figures.

DETAILED DESCRIPTION

Figure 1:
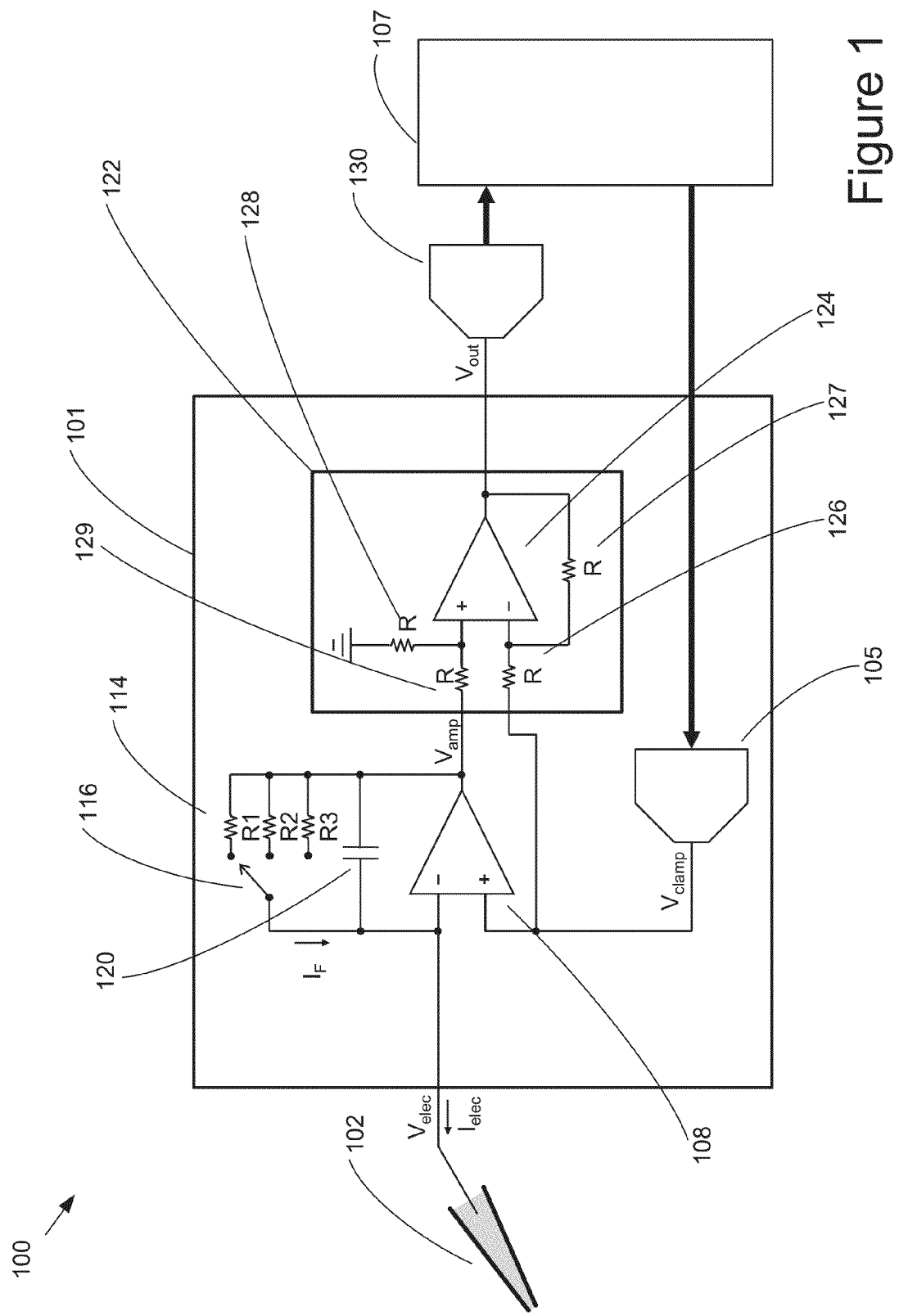
FIG. 1 illustrates an example of a conventional patch-clamp amplifier, in accordance with some embodiments.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction:

Patch-clamp electrophysiology has been a central tool of neuroscience and pharmaceutical research since its advent in the late 1970s. Patch-clamping utilizes glass micropipettes and sensitive analog electronics to monitor the ion channel currents of individual neurons or other electrically active cells. Micropipettes are constructed by heating the center of a glass capillary tube until the glass begins to melt and pulling the ends apart in a controlled fashion. This creates two hollow micropipettes whose diameters taper from several millimeters at the non-melted end to approximately one micrometer at the end that was exposed to heat. The micropipette is filled with a conductive electrolyte solution, and a metal wire is inserted into the large end so that it conducts electrical current from the solution. This wire is connected to a patch-clamp amplifier that holds the voltage of the electrode at a particular level referred to as the clamp voltage, which is a voltage that remains substantially constant throughout the measurement process or until a different voltage is used. In this context, substantially constant may indicate that the voltage does not vary, or only varies negligibly with respect the measurements being made. The patch-clamp amplifier may be used to measure the current flowing through the electrode.

Traditionally, highly trained scientists or technicians use micromanipulators and a microscope to guide the micropipette electrode so that the 1-micrometer opening contacts a tiny "patch" of cell membrane in a cell culture or other piece of living tissue. The application of weak suction holds the cell to the micropipette electrode tip and forms a high-resistance "gigaseal" typically having a resistance greater than one gigaohm to the surrounding extracellular fluid. In some patch-clamp experiments, the small patch of cell membrane underneath the electrode is pulled away from the rest of the cell and studied in isolation. In other "whole cell" experiments, additional suction or high-voltage pulses are used to puncture the small patch of cell membrane and provide electrical access to the interior of an entire cell. In either case, the patch-clamp amplifier is used in "voltage clamp" mode to hold or "clamp" the electrode voltage at desired levels and then measure the resulting current flowing through the electrode under various conditions (e.g., when the voltage is changed to a new level, when various chemicals are applied to the tissue, or when other stimuli are applied to the tissue). The return path for the current is often provided by an Ag/AgCl or Pt wire placed in the tissue nearby.

In the last ten years, advances in automation have led to the development of inexpensive robotic systems capable of automatically patch-clamping many cells in minutes, with success rates matching or exceeding those of skilled technicians. As a result of this innovation, patch-clamp techniques are being adapted to a wider variety of experimental protocols and target species, and researchers are now recording electrical activity from multiple cells simultaneously. However, the size and expense of the traditional patch-clamp amplifier electronics presents a significant bottleneck to the continued development of large-scale highly automated intracellular recording systems. Traditional patch-clamp amplifiers capable of voltage-clamp measurements are large rack-mounted boxes weighing several kilograms and costing nearly $10,000 per channel. These instruments represent the dominant component of modern patch-clamp recording systems in terms of size, mass, and cost. The move to multi-channel automated systems will only exacerbate this problem.

Current Sensing Patch-Clamp Amplifier Systems and Methods:

Traditional patch-clamp amplifiers are transimpedance amplifiers using extremely high-valued resistors (in the range of 10 MΩ to 50 GΩ) to convert small ion channel currents into sufficiently large voltages to permit sampling by an analog-to-digital converter (ADC). Resistors in the high megohm to gigaohm range are very difficult to miniaturize and integrate onto microchips; this has been a barrier to miniaturization of high quality patch-clamp amplifiers. Typical microchip fabrication processes provide circuit designers a form of polysilicon that can be placed in long thin strips to create on-chip resistors. Even fabrication processes optimized for analog circuits provide only moderately resistive polysilicon that can be used to create resistors in the kilohm range, but not the gigaohm range. Larger resistors may be made by allocating large amounts of chip area to a thin, serpentine strip of polysilicon, but resistors created in this way have significant parasitic capacitances to the chip substrate. These capacitances limit the bandwidth of any circuits using these resistors and may reduce the stability of feedback circuits. Moreover, resistors made in this way occupy a substantial amount of space on the chip, thus reducing the ability to miniaturize the entire patch-clamp amplifier.

These parasitic capacitances may be reduced by using a silicon-on-insulator (SOI) or silicon-on-sapphire (SOS) fabrication process, but these processes are relatively rare and more expensive that mainstream silicon fabrication processes. Even if the parasitic capacitances of large on-chip resistors are reduced using exotic fabrication technologies, these resistors still consume large amounts of chip area and thus increase the cost of the chip. On-chip resistors in the megohm range are currently possible to fabricate on chip if large amounts of chip area are allocated to a single device, but linear resistors in the gigaohm range are too large for any practical microchip.

This requirement for large-valued feedback resistors has prevented entire patch-amplifiers from being completely integrated on a chip. Typically the feedback resistor is placed off chip. Often, the off-chip gigaohm resistor is nearly the same size as the chip containing all the other electronics. Placing the feedback resistor off chip has a further disadvantage beyond size: various contaminants including residual solder flux, oil from fingers, or even humid air can create parasitic resistances in the gigaohm range on a circuit board. These parasitic resistances provide additional paths for small currents to flow, and this can adversely affect the precision of a current sensing circuit that relies on a precise feedback resistance. To reduce circuit size and provide immunity to off-chip parasitic resistances it is desirable to integrate the entire patch-clamp current measurement circuit onto a single microchip.

In various embodiments disclosed herein, feedback transistors are used as nonlinear circuit elements to convert a small current into a logarithmically encoded voltage. These feedback transistors occupy little chip area and are sensitive across many orders of magnitude from picoamps to nanoamps, spanning the entire range of physiologically relevant currents. Representing the measured current logarithmically also eliminates the need for switching between different current measurement ranges. Moreover, the patch-clamp current measurement circuit in which the feedback transistors are implemented may also include or be coupled to calibration circuitry which may be configured to calibrate the entire current measurement circuit based on the operating conditions and parameters of the feedback transistors. In this way, feedback transistors may be used as a feedback circuit for an operational amplifier while maintaining a high fidelity of accuracy in the resulting current measurements.

When metal-oxide-semiconductor field-effect transistors (MOSFETs) operate with currents in the picoamp or nanoamp range, they exhibit an exponential relationship between drain current and gate-to-source voltage. Bipolar transistors also operate with an exponential relationship between collector current and base-to-emitter voltage. Either transistor may be used in the feedback circuit described herein. The output of an op amp may be tied to the gate of a transistor, and the transistor's source may be tied to ground. The drain current of the transistor may be fed into a current mirror, and this mirrored current may be fed back to the negative input of the op amp. This structure may be provided using n-channel transistors and p-channel transistors so that both positive and negative currents may be measured.

The op amp's negative feedback ensures that the transistor gate will be driven to a voltage that causes the transistor to pass a current equal to the current flowing through the electrode, which may be connected to the negative input of the op amp. The voltage on the transistor gate is taken as the output of the patch-clamp amplifier. The output voltage may encode the electrode current logarithmically. The output voltage may be converted to a digital number by an analog-to-digital converter (ADC), and a computer or other digital controller may calculate the electrode current using a transistor current-voltage equation disclosed herein.

As similarly discussed above, the accuracy of the current measurement may be improved by measuring two or more known currents and using these measurements to calculate parameters used in the current-to-voltage relationship. Additionally, a temperature sensor may be placed near the patch-clamp amplifier and used to sense significant temperature changes that could be used to trigger a re-measurement and recalculation of transistor parameters.

Accordingly, various systems and method disclosed herein provide integration of all electronics included in a patch-clamp amplifier onto a small, low-power, inexpensive microchip. In various embodiments, a microchip may refer to a silicon die or a circuit board capable of being configured to implement one or more circuits disclosed herein. It will be appreciated that a chip or microchip as referred to herein may refer to any die or board in which an electrical circuit may be implemented. When implemented on a single chip, fully integrated patch-clamp amplifiers can be mounted in close proximity to each micropipette in a large-scale automated recording system, reducing noise pickup, size, and cost. In this way, the size and cost of patch-clamp amplifier systems is reduced and may be effectively scaled up for large-scale operations.

For example, the large rack-mount systems previously described and used in laboratory settings may be reduced to a circuit that may be implemented on a single chip and that is far cheaper than a rack-mount system. Moreover, large scale operations, such as drug screening, may be performed cheaper and more efficiently because each channel used to make measurements is cheaper and is more compatible with the automated hardware, such as robotic arms, used to make the measurements due to the decreased size and bulk of the microchip itself.

These and other features of the present invention will be presented in more detail in the following specification of embodiments and the accompanying figures which illustrate by way of example the principles of the embodiments. While a preferred embodiment may be described, it is not intended that the present invention be limited to the described embodiment. It is intended that the invention cover all modifications and alternatives which may be included within the spirit and scope of the invention.

FIG. 1 illustrates an example of a conventional patch-clamp amplifier, in accordance with some embodiments. Circuit 100 may include patch-clamp amplifier 101 which may be used to clamp electrode 102 at a specified clamp voltage, $V_{CLAMP}$, and may be further used to measure the resulting electrode current. Operational amplifier ("op amp") 108 may be used as a transimpedance amplifier to convert the small electrode current, which may be in the range of 1 picoamp to 100 nanoamps, to a larger amplified voltage, which may be in the range of 1 millivolt to 10 volts. In conventional methods, op amp 108 uses field effect transistor (FET) devices at its input terminals so that current flowing into either input terminal of op amp 108 is significantly less than one picoamp in magnitude.

If the current flowing into the negative input terminal of op amp 108 is negligible compared with the electrode current, $I_{ELEC}$, then a feedback current flowing through a fed back resistor, such as the feedback current, $I_F$, that flows through feedback resistor 114, will be equal to the electrode current. In circuit 100, feedback resistor 114 is comprised of several resistors of varying values. As discussed in greater detail below, feedback resistor 114 is a conventional feedback resistor. Thus, feedback resistor 114 is too large to be implemented on-chip, and is located off-chip. Accordingly, while FIG. 1 illustrates feedback resistor 114 as being part of patch-clamp amplifier 101, it will be appreciated that feedback resistor 114 is located remotely and off-chip. The feedback current and the electrode current may be determined and/or related to each other based on the following equation:

$$I_F = I_{elec}.$$

The voltage at the positive input of op amp 108 may be set by a voltage source at a predetermined voltage, such as clamp voltage $V_{CLAMP}$, which will typically have a value within the range of ±1V. The voltage source may be implemented as digital-to-analog converter (DAC) 105 that is controlled by a computer system or digital controller 107.

Op amp 108 produces an output voltage, $V_{AMP}$, that is equal to the difference between the voltage at the positive input of op amp 108 and the voltage at the negative input of op amp 108 multiplied by a large gain (typically between 1,000 and 1,000,000). By connecting the output of op amp 108 to its negative input through a feedback resistor, such as feedback resistor 114 which may have a value of R1, R2, or R3 as selected by switch 116, op amp 108 provides feedback that creates a "virtual ground" between its two inputs and holds the electrode voltage 118 at nearly the same potential as the positive input of op amp 108. Thus, the electrode voltage may be determined based on the following equation:

$$V_{elec} = V_{clamp}.$$

The resulting voltage at the output of op amp 108, $V_{AMP}$, is equal to the combination of the voltage at the negative input of op amp 108, and the voltage drop across the selected feedback resistor. Thus, the voltage at the output of op amp 108 may be determined based on the following equation:

$$V_{amp} = V_{elec} + I_F R_F = V_{clamp} + I_{elec} R_F.$$

Feedback capacitor 120 attenuates high-frequency noise in circuit 100 and helps to keep the feedback stable. Feedback capacitor 120 may have a small value that is between 10 femtofarads and 100 picofarads.

Circuit 100 may also include difference amplifier 122 that may be a standard difference amplifier implemented using op amp 124 and four identically-valued resistors R, such as resistors 126-129, which may have a value between 1 kilohm and 1 megohm. Op amp 124 of difference amplifier 122 may subtract the two voltages $V_{AMP}$ and $V_{CLAMP}$ and produce an output voltage, $V_{OUT}$, at the output of difference amplifier 122. The output voltage of difference amplifier 122 may be determined based on the following equation:

$$V_{out} = V_{amp} - V_{clamp} = I_{elec} R_F.$$

Accordingly, the output voltage of patch-clamp amplifier 101 is a voltage that is proportional to the current flowing into electrode 102 and feedback resistor 114, the value of which may be used to set a scale for currents and voltages in circuit 100. Since the electrode current can vary by many orders of magnitude in different patch-clamp experiments (for example, currents may range from 1 pA to 100 nA), feedback resistor 114 may have different values, such as R1, R2, and R3 shown in FIG. 1. An appropriate value for feedback resistor 114 may be selected based on a position or configuration of switch 116. The value of feedback resistor 114 may be selected based on a preferred current measurement for a particular experiment or application.

In order to provide a voltage that may be captured by analog-to-digital converter 130, feedback resistor 114 typically has a large value, such as a value exceeding 10 megaohms. The large resistance value of feedback resistor 114 may convert very small electrode currents into voltages sufficiently large to be captured by analog-to-digital converters. If the electrode current is in the range of picoamps, feedback resistor 114 may have a resistance value that exceeds 1 gigaohm. As previously discussed above, resistors having the large values typically associated with feedback resistor 114 in a conventional patch-clamp circuit cannot be integrated onto a microchip because they are too large. Accordingly, a conventional patch-clamp amplifier represented by circuit 100 cannot be effectively miniaturized, and is often impractical for laboratory and commercial purposes due to the high cost and bulk associated with the additional and off-chip circuitry.

Figure 2:
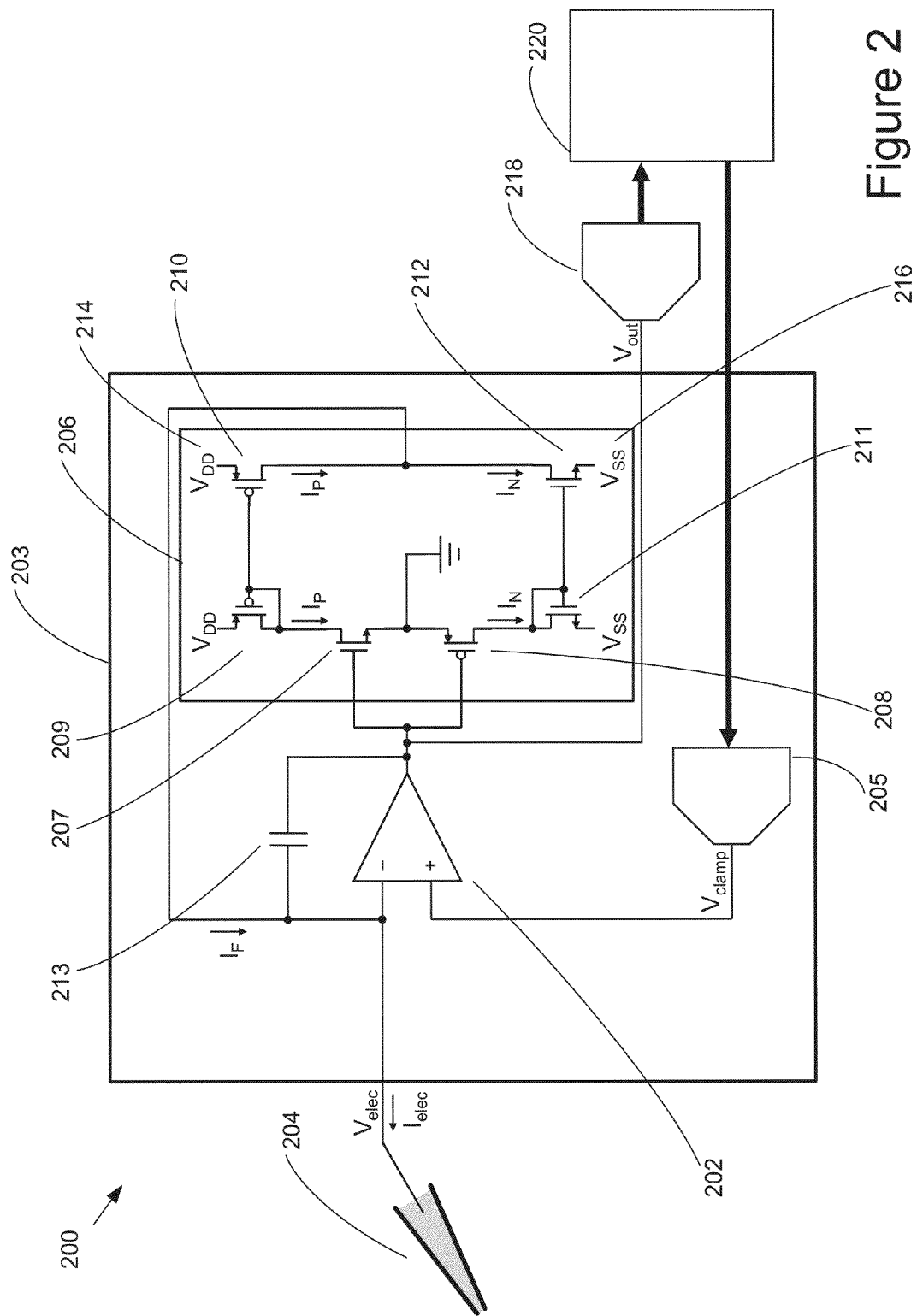
FIG. 2 illustrates an example of a patch-clamp amplifier that includes a transistor-based feedback circuit, in accordance with some embodiments.

FIG. 2 illustrates an example of a patch-clamp current measurement circuit that includes a transistor-based feedback circuit, in accordance with some embodiments. Current measurement circuit 200 may be configured to include op amp 202, which may be a FET-input op amp. Current measurement circuit 200 may be further configured to provide op amp 202 with negative feedback to set the voltage of electrode 204, $V_{ELEC}$, to a clamping voltage, $V_{CLAMP}$, which may be produced by digital-to-analog converter 205. Current measurement circuit 200 may also include digital-to-analog converter 205, analog-to-digital converter 218, and digital controller 220. In some embodiments, one or more of digital-to-analog converter 205, analog-to-digital converter 218, and digital controller 220 may be implemented in electrical components or chips that are separate from patch-clamp amplifier 203. In various embodiments, one or more of digital-to-analog converter 205, analog-to-digital converter 218, and digital controller 220 may be implemented on the same chip as patch-clamp amplifier 203 which, as previously discussed, may be a silicon die, or a silicon chip soldered or coupled to a generic circuit board. Thus, a single chip may include all components of current measurement circuit 200 and provide a compact and inexpensive package that includes all components of current measurement circuit 200 as on-board components.

Figure 3:
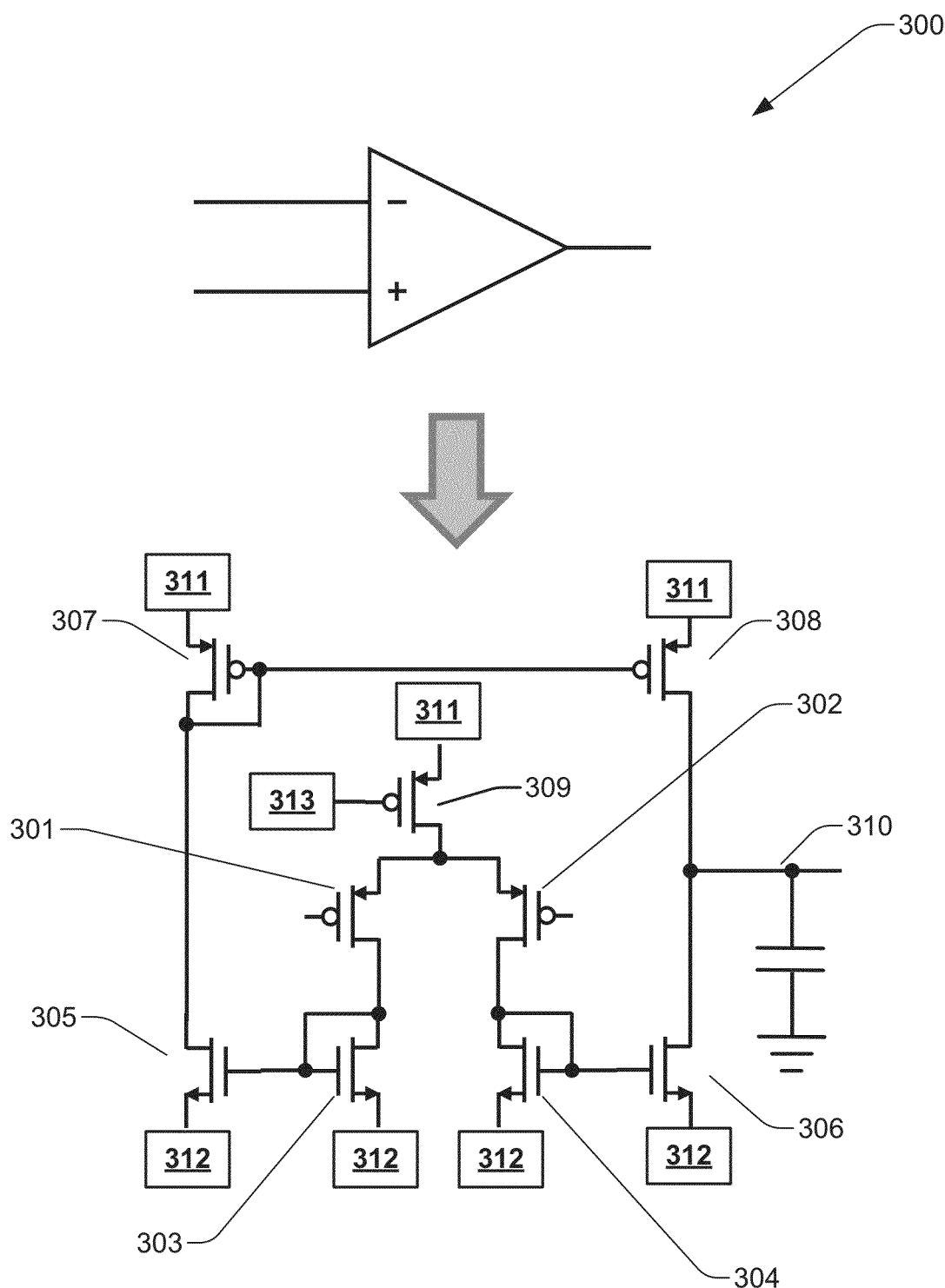
FIG. 3 illustrates an example of a field-effect transistor (FET)-input op amp, implemented in accordance with some embodiments.

An example of a configuration of transistors which may be used to create op amp 202 is illustrated in FIG. 3. Accordingly, FIG. 3 illustrates an example of a field-effect transistor (FET)-input op amp, implemented in accordance with some embodiments. FET-input op amp 300 may include one or more metal-oxide-semiconductor field-effect transistors (MOSFETs), such as devices 301-309, and may be coupled to power sources, such as positive power source 311, negative power source 312, and bias voltage 313. As shown in FIG. 3, the input terminal and output terminal of FET-input op amp 300 are coupled to the gates of device 301 and device 302 respectively. An output voltage generated at node 310, which may be an output terminal FET-input op amp 300, represents a difference between the input and output voltage at devices 301 and 302, respectively, multiplied by a gain, as discussed in greater detail below with reference to FIG. 2. While FIG. 3 illustrates one example of a FET-input op amp, it will be appreciated that other configurations are possible and within the scope of the subject matter disclosed herein.

Returning to FIG. 2, current measurement circuit 200 may be configured to include transistor circuit 206. In various embodiments, transistor circuit 206 may be a feedback circuit that includes several transistor devices configured to generate a positive feedback current and/or negative feedback current based on an output voltage at the output terminal of op amp 202. Transistor circuit 206 may include a first set of transistor devices configured to generate a positive feedback current for positive output voltages. Transistor circuit 206 may further include a second set of transistor devices configured to generate a negative feedback current for negative output voltages. For example, the first set of transistor devices may include a first transistor device, such as device 207 discussed in greater detail below, that may have a controlling terminal, such as a gate, coupled to the output terminal of op amp 202. The first transistor device may generate a first feedback current that is an exponential function of a voltage value at the output terminal. Additional transistor devices in the first set of transistor devices may be configured to provide a positive current mirror that mirrors the first feedback current to generate a positive feedback current. An output of the positive current mirror may be coupled to an input of op amp 202, thus providing feedback to op amp 202. In this way, the first set of transistor devices may be configured to generate a positive feedback current that is an exponential function of an output voltage of op amp 202. The positive feedback current may be fed back to an input terminal of op amp 202. Similarly, a second set of transistor devices may include a second transistor device, such as device 208, configured to generate a second feedback current that is mirrored by a negative current mirror to generate a negative feedback current. The output of the negative current mirror may be coupled to an input terminal of op amp 202 to provide the negative feedback current to op amp 202.

Furthermore, as discussed in greater detail below, the first transistor device and the second transistor device may be coupled to a circuit ground, thus referencing the output voltage of op amp 202 to ground. For example, a source or emitter for each of the first transistor device and the second transistor device may be coupled to the circuit ground. Configuring the first transistor device and the second transistor device in this way simplifies the circuitry implemented in current measurement circuit 200 because a clamp voltage, $V_{CLAMP}$, does not need to be subtracted from the output voltage of op amp 202. Moreover, coupling the source or emitter for the first transistor device and the second transistor device to ground also eliminates variances in the operation of the first transistor device and the second transistor device which may occur due to the body effect, thus resulting in greater accuracy during subsequent calculation of the electrode current.

Thus, instead of a feedback resistor, as described previously with reference to circuit 100 of FIG. 1, a feedback current, $I_F$, may be provided by transistor circuit 206. In some embodiments, transistor circuit 206 is constructed from one or more MOSFETs. As shown in FIG. 2, transistor circuit 206 includes six transistor devices; devices 207-212. In various embodiments, current measurement circuit 200 also includes feedback capacitor 213, which may couple the output and negative input of op amp 202 to attenuate high frequency noise and stabilize the feedback loop created by transistor circuit 206.

In some embodiments, devices 207, 211, and 212 are n-channel MOSFETs. An n-channel MOSFET may be a MOSFET that may include a p-type semiconductor capable of forming an n-type channel between the MOSFET's source and drain in response to receiving a sufficient voltage at the MOSFET's gate. Devices 208, 209, and 210 may be p-channel MOSFETs. A p-channel MOSFET may be a MOSFET that includes an n-type semiconductor capable of forming a p-type channel between the MOSFET's source and drain in response to receiving a sufficient voltage at the MOSFET's gate. Transistor circuit 206 may be powered by two DC voltage supplies. For example, as shown in current measurement circuit 200, transistor circuit 206 may be powered by first voltage source 214, $V_{DD}$, which may be in the range of +0.5 V to +5.0 V. Transistor circuit 206 may also be powered by second voltage source 216, $V_{SS}$, which may be in the range of −0.5 V to −5.0 V. While examples of voltage ranges are disclosed herein, it will be appreciated that other voltage ranges may be used as well.

In some embodiments, devices 211 and 212 form an n-channel MOSFET current mirror. Thus, the current mirror generated by devices 211 and 212 detects or senses the current flowing into the drain of device 211, $I_N$, and generates an identical current flowing into the drain of device 212. In various embodiments, devices 209 and 210 form a p-channel MOSFET current mirror. The current mirror generated by devices 209 and 210 detects or senses the current flowing out of the drain of 209, $I_P$, and generates an identical current flowing out of the drain of device 210. In various embodiments, the outputs of the two current mirrors created by devices 207-212 are tied together.

While FIG. 2 illustrates one example of a configuration of transistors that may be used to create a current mirror, it will be appreciated that any configuration of transistors capable of creating a current mirror may be used. For example, each current mirror may include 4 or 8 transistors. Accordingly, the output current of the two current mirrors produces a feedback current, $I_F$, as determined by the equation:

$$I_F = I_P - I_N$$

The current $I_P$ is determined by the gate-to-source voltage of device 207 which, as previously discussed, may be an n-channel MOSFET. When passing currents in the picoamp or nanoamp range, an n-channel MOSFET may operate in a subthreshold mode; also known as weak inversion. In this region of operation, the drain current $I_D$ of a MOSFET transistor may be determined based on the following equation:

$$I_D = I_0 e^{(V_G - V_S)/nV_T}$$

In this equation, $I_0$ is a device constant typically in the range of $10^{-25}$ A to $10^{-5}$ A, n is a device constant typically in the range of 1 to 2, $V_T$ is the thermal voltage kT/q (where k is Boltzmann's constant, T is absolute temperature in Kelvin, and q is the unit charge of an electron), $V_G$ is the MOSFET gate voltage and $V_S$ is the MOSFET source voltage. As applied to current measurement circuit 200, the gate of device 207 is coupled to the output of op amp 202 and the source of device 207 is coupled with ground. Thus, the equation for the drain current of device 207 which, as previously discussed, is denoted as $I_P$, may be written as:

$$I_P = I_0 e^{V_{out}/nV_T}$$

Thus, the drain current of device 207 may be an exponential function of the output voltage, $V_{OUT}$, of op amp 202. The drain current may be mirrored by devices 209 and 210, and fed back to the negative input of op amp 202. If $V_{OUT} > 0$, device 208, which may be a p-channel MOSFET, will have a negligible drain current. Accordingly, in this situation, $I_N = 0$ and $I_F = I_P$. In the case where op amp 202, which may be a FET-input op amp, has negligible current flowing into its input terminals, $I_F = I_{ELEC}$, and the relationship between $I_{ELEC}$ and $V_{OUT}$ may be expressed as the following equation:

$$I_{elec} = I_0 e^{V_{out}/nV_T} \quad \text{[First equation]}$$

Solving for $V_{OUT}$ yields a second equation:

$$V_{out} = nV_T \ln \frac{I_{elec}}{I_0}. \quad \text{[Second equation]}$$

Accordingly, the output voltage $V_{OUT}$ of op amp 202 and patch-clamp amplifier 203 is a logarithmic function of the electrode current $I_{ELEC}$. This logarithmic encoding of current is advantageous because electrode currents spanning many orders of magnitude (e.g., from 1 pA to 100 nA) are represented in a relatively narrow range of voltages. If a high-resolution analog-to-digital converter (e.g., 16- to 24-bit resolution) is used to digitize $V_{OUT}$ and a computer system or digital controller 220 calculates the electrode current based on this logarithmic encoding, then $I_{ELEC}$ can be sensed with high fidelity. This captures a wide range of currents without requiring the user to select a particular measurement range by switching to different feedback resistors (e.g., using switch 116 included in circuit 100 of FIG. 1).

The first and second equations shown above describe the situation where current is flowing out of electrode 204 and into a cell or tissue (i.e., positive electrode currents) that may be attached or coupled to current measurement circuit 200. In this situation, $V_{OUT}$ will be greater than zero, device 207 will be on, and device 208 will be off. In the situation where current is flowing in the other direction (i.e., negative electrode currents), $V_{OUT}$ will be less than zero, device 207 will be off, and device 208 will be on. In this situation, the drain current $I_N$ of device 208 may be determined based on the following equation:

$$I_N = I_0 e^{-V_{out}/nV_T} \quad \text{[Third equation]}$$

In this situation, device 207 is off, and $I_P = 0$. Therefore, $I_F = -I_N$, and the relationship between $I_{ELEC}$ and $V_{OUT}$ may be expressed as the following equation:

$$I_{elec} = -I_0 e^{-V_{out}/nV_T}$$

Solving for $V_{OUT}$ yields the following equation:

$$V_{out} = -nV_T \ln \frac{-I_{elec}}{I_0}. \quad \text{[Fourth equation]}$$

As similarly discussed above, negative output voltages encode negative electrode currents logarithmically in the same way that positive output voltages encode positive electrode currents logarithmically.

In various embodiments, current measurement circuit 200 does not require a difference amplifier. Thus, in contrast to conventional patch-clamp amplifiers, such as the patch-clamp amplifier shown in circuit 100 of FIG. 100, patch-clamp amplifier 203 disclosed herein does not require a difference amplifier to subtract $V_{CLAMP}$ from the output voltage of op amp 108. The reduced circuit complexity disclosed herein is advantageous because the total amount of circuitry and power consumption associated with the patch-clamp amplifier is reduced, thus facilitating miniaturization of the circuit and implementation in a microchip environment. Moreover, the reduced circuitry afforded by the removal of the difference amplifier also reduces the possibility of additional stray currents deleteriously affecting measurements obtained from patch-clamp amplifier 203 and results in more accurate measurements.

Some conventional patch-clamp amplifiers have used non-linear feedback elements, such as diodes and transistors, to convert currents into voltages. However, these nonlinear feedback elements are directly connected from the output of the op amp to its negative input. In various embodiments, the patch-clamp amplifiers described herein use transistors, such as devices 207 and 208, with sources coupled to ground, thus ensuring that the resulting output voltage is referenced to ground, and not to $V_{CLAMP}$. As similarly discussed above, by referencing the output voltage to ground, the difference amplifier may be eliminated from the circuit, thus simplifying the circuitry within the patch-clamp amplifier and facilitating miniaturization of the circuit for implementations in a microchip environment. Furthermore, referencing the output voltage to ground makes the voltage-to-current transformation performed by devices 207 and 208 more accurate because the body effect which may be associated with transistor devices is eliminated. The body effect is a phenomenon where various transistor parameters change when the source voltage moves with respect to the chip substrate (which is typically tied to a voltage source, such as second voltage source 216 $V_{SS}$). By coupling the sources of devices 207 and 208 to ground, their source-to-substrate voltage is kept constant, so the body effect is eliminated and does not interfere with the processing methods disclosed herein which may be implemented to reconstruct the electrode current based on the output voltage $V_{OUT}$.

In various embodiments, current measurement circuit 200 may also be implemented using bipolar junction transistors (BJTs) instead of MOSFETs. In the configuration where the transistor devices are BJT transistors, device 207 may be an npn transistor, and device 208 may be a pnp transistor. The first through fourth equations described above would continue to apply because bipolar transistors also have an exponential relationship between voltage and current.

According to various embodiments, the output voltage $V_{OUT}$ may be sampled by analog-to-digital converter 218. Thus, analog-to-digital converter 218 may be coupled or connected to an output port of patch-clamp amplifier 203 and may sample an output signal identifying an output voltage provided at the output port. The sampled output voltage may be converted to an equivalent electrode current by performing calculations in accordance with the first equation if the output voltage $V_{OUT}$ is positive, or by performing calculations in accordance with the third equation if the output voltage $V_{OUT}$ is negative.

The accuracy and ability to perform these calculations depends on the accuracy of the values of the constants $I_0$, n, and $V_T$, which may be associated with transistors such as devices 207-212. Thus, according to various embodiments, a calibration process may be utilized to ensure that the appropriate values are being used to process the measurements taken by patch-clamp amplifier 203, and to further ensure that the electrode current is being calculated accurately. As previously discussed, of the values of $J_0$, n, and $V_T$ should be as accurate as possible to ensure that the calculated electrode current is accurate. Because n is multiplied by $V_T$ in the previously described equations, an accurate value for the product $nV_T$ is sufficient. The values for $J_0$ and $nV_T$ may be calculated by using patch-clamp amplifier 203 represented in current measurement circuit 200 to measure two known currents $I_{KNOWN1}$ and $I_{KNOWN2}$, to generate two output voltages $V_{OUT1}$ and $V_{OUT2}$. From the previously described first equation, the following formulas may be derived:

$$I_{known1}I_0 e^{V_{out1}/nV_T}.\qquad\text{[Fifth equation]}$$

$$I_{known2}I_0 e^{V_{out2}/nV_T}.\qquad\text{[Sixth equation]}$$

Figure 7A:
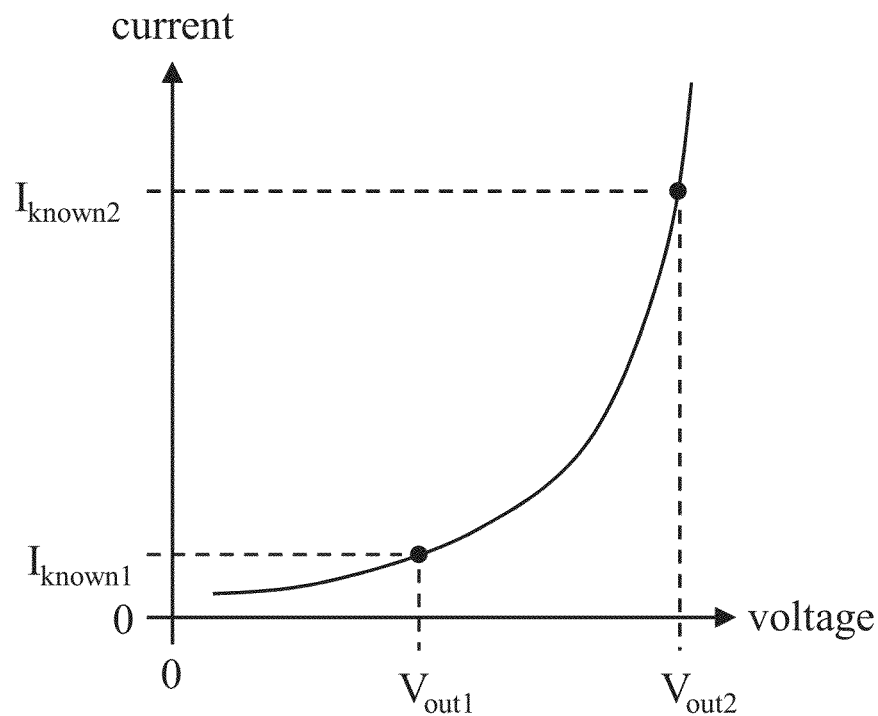
FIG. 7A illustrates an exponential current-voltage curve that includes two data points associated with two known currents used to calibrate a patch-clamp amplifier, in accordance with some embodiments.

FIG. 7A illustrates an exponential current-voltage curve that includes two data points associated with two known currents used to calibrate a patch-clamp amplifier, in accordance with some embodiments. If the natural logarithm is taken for both sides of the fifth and sixth equations, these exponential equations may be transformed into linear functions of voltage, as expressed in the following equations:

$$\ln I_{known1} = nV_T V_{out1} + \ln I_0 \qquad\text{[Seventh equation]}$$

$$\ln I_{known2} = nV_T V_{out2} + \ln I_0 \qquad\text{[Eighth equation]}$$

As discussed in greater detail below with reference to FIG. 7B, once expressed as linear functions, various mathematical characteristics of the line created by the two data points may be used to determine the values of one or more thermal constants associated with transistor devices included in the current measurement circuit.

Figure 7B:
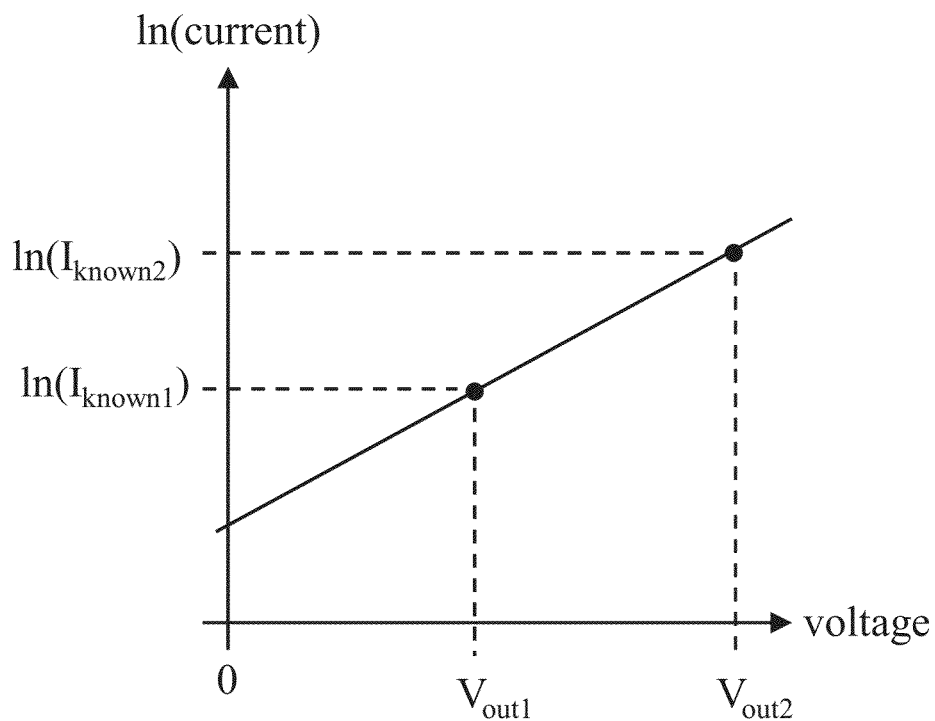
FIG. 7B illustrates a current-voltage curve that uses a logarithmic current axis, in accordance with some embodiments.

FIG. 7B illustrates a current-voltage curve that uses a logarithmic current axis, in accordance with some embodiments. The slope of the line in the graph illustrated in FIG. 7B corresponds to $nV_T$, and the y-intercept corresponds to $\ln(I_0)$.

The two measurements of the known currents comprise two data points that are sufficient to solve for the two unknowns $J_0$ and $nV_T$ based on one or more algebraic operations. Once the values of these two parameters are calculated, any value of $V_{OUT}$ may be converted to a corresponding electrode current $I_{ELEC}$ with high accuracy. In this way, the electrode current may be determined or reconstructed accurately because the processing operations performed on measurements obtained from the current measurement circuit have been calibrated and adjusted specifically for the current operating conditions of the transistor devices included in the current measurement circuit.

While various embodiments described herein have been described as using two known currents, it will be appreciated that for additional accuracy, more than two known currents may be measured. For example, 4 or 8 known currents may be used to obtain additional measurements and data points. Standard linear regression techniques may be used to fit a line to the resulting data points and to determine values for $I_0$ and $nV_T$ which may be used for subsequent calculations of electrode currents based on measured output voltages.

Furthermore, the calibration process may also utilize both positive and negative known currents. Thus, a calibration process may be performed for each current mirror. As previously discussed, device 207 may be an n-channel transistor and device 208 may be a p-channel transistor 208. Thus, device 207 and 208 may have different values of $J_0$ and $nV_T$. Accordingly, the calibration procedure may use two or more known positive currents and two or more known negative currents to determine values of $J_0$ and $nV_T$ for both the n-channel transistor and the p-channel transistor.

Figure 4:
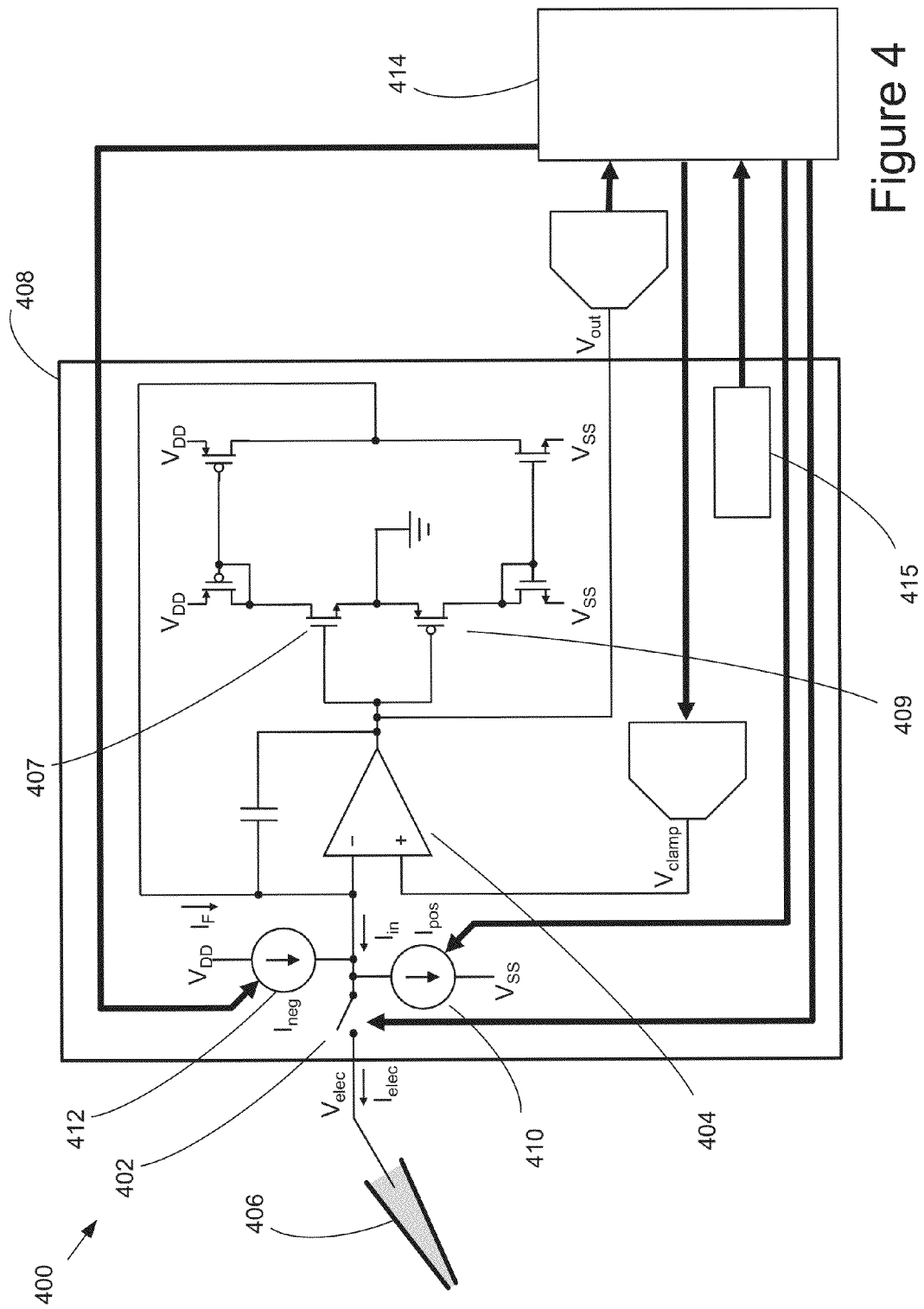
FIG. 4 illustrates an example of a patch-clamp current measurement circuit that may be calibrated by a first calibration circuit, in accordance with some embodiments.

FIG. 4 illustrates an example of a patch-clamp current measurement circuit that may be calibrated by a first calibration circuit, in accordance with some embodiments. The first calibration circuit may include one or more current sources which may be coupled to patch-clamp amplifier 408. The current sources may be used to calibrate patch-clamp amplifier 408 in accordance with one or more of the calibration methods described above with reference to FIGS. 2, 7A, and 7B, and also below with reference to FIG. 8. Accordingly, current measurement circuit 400 may include switch 402 which may be a single MOSFET, or may be a complementary MOSFET (CMOS) transmission gate. Switch 402 may be used to isolate op amp 404 from electrode 406 during circuit calibration. Thus, switch 402 may be configured to switch from a first state in which electrode 406 is electrically coupled to op amp 404 included in patch-clamp amplifier 408, to a second state in which electrode 406 is not electrically coupled to op amp 404 included in patch-clamp amplifier 408. In various embodiments, the first calibration circuit may include or may be coupled to first current source 410, which may be a positive current source $I_{POS}$, and second current source 412 which may be a negative current source $I_{NEG}$. In some embodiments, first current source 410 and second current source 412 are programmable current sources controlled by a computer system or digital controller 414.

In some embodiments, first current source 410 and second current source 412 are configured to perform calibration operations sequentially as part of calibration process. For example, in a first phase of calibration, second current source 412 may be set to zero while first current source 410 is set to provide a first known positive current $I_{KNOWN1}$. Thus, in the first phase of calibration, op amp 404 in patch-clamp amplifier 408 may receive the first known positive current instead of an electrode current associated with electrode 406. In response to receiving the first known positive current, patch-clamp amplifier 408 may be configured to generate a first positive output voltage $V_{OUT1}$ that is digitized and recorded by the computer system or digital controller 414 that is controlling the first calibration circuit and patch-clamp amplifier 408. First current source 410 may also be configured to provide a second known positive current $I_{KNOWN2}$ to patch-clamp amplifier 408. In response to receiving the second known positive current, patch-clamp amplifier 408 may be configured to produce a second positive output voltage $V_{OUT2}$ that is digitized and recorded by the computer or digital controller 414. Based on the first and second positive output voltages, and based on the seventh and eighth equations discussed above, the parameters $I_0$ and $nV_T$ may be determined for device 407. As similarly discussed above, more than two known currents may be used to obtain multiple data points. For example, four known currents may be provided to patch-clamp amplifier 408. A regression analysis of four positive output voltages produced in response to receiving the four known positive currents may determine the parameters $I_0$ and $nV_T$.

Once the first phase of calibration has been completed, a second phase of calibration may be performed. In the second phase of calibration, first current source 410 may be set to zero while second current source 412 may be set to provide a first known negative current to patch-clamp amplifier 408. As similarly discussed above with reference to the first phase of calibration, patch-clamp amplifier 408 may generate a first negative output voltage in response to receiving the first known negative current. The first negative output voltage may be digitized and recorded by a computer system or digital controller 414. This may be repeated for a second known negative current to produce a second output voltage that is also digitized and recorded by the computer system or digital controller 414. The measurements may be repeated for any number of known currents. The measurements may be used to solve for or approximate the parameters $I_0$ and $nV_T$ for device 409. Once the calibration process is complete and the parameters $I_0$ and $nV_T$ have been accurately determined, subsequently measured electrode currents may be calculated or reconstructed accurately based on measured output voltages.

In various embodiments, the calibration process may be performed automatically when current measurement circuit 400 receives power or is turned on. Furthermore, the calibration process may also be performed automatically in response to a thermal sensor, such as temperature sensor 415, generating an output, as discussed in greater detail below with reference to FIG. 6. Thus, digital controller 414 may be configured to automatically execute one or more calibration operations in response to current measurement circuit 400 receiving power, as indicated by a power signal or power line, and/or in response to temperature sensor 415 generating an output identifying a sufficient deviation in one or more thermal characteristics of the transistor devices included in current measurement circuit 400. In various embodiments, instead of automatically executing the one or more calibration operations, a notification may be generated that notifies a user that calibration of current measurement circuit 400 should be performed. Accordingly, instead of automatically calibrating current measurement circuit 400, digital controller 414 may be configured to generate a notification in response to current measurement circuit 400 receiving power and/or in response to receiving a signal from temperature sensor 415. The generated notification may be provided to a computer system and displayed at a display device of the computer system.

In some embodiments, digital controller 414 may be further configured to determine whether an automatic calibration should be performed or whether a notification should be generated. Digital controller 414 may make this determination based on whether or not a cell is coupled to electrode 406. For example, based on an impedance measurement taken at electrode 406, digital controller 414 may determine that a cell is coupled to electrode 406 and that a notification should be generated because current measurement circuit 400 should not be calibrated while a cell is coupled with electrode 406.

In various embodiments, first current source 410 and second current source 412 may be configured to introduce a direct current (DC) offset. In experimental conditions, an electrode current may change from a positive current to a negative current. For example, switching the magnitude or sign of the clamping voltage $V_{CLAMP}$ may cause the electrode current to switch between a positive and a negative value. For example, the polarity of the current may oscillate in a range of 100 Hz to 1000 Hz depending on activity within the cell attached to the electrode. When the electrode current changes from a positive to a negative value, the output voltage of op amp 404 may swing by more than 1 V as it moves from a positive output voltage to a negative output voltage. In various embodiments, op amp 404 has a finite slew rate that limits the speed at which the output voltage may transition from a positive to a negative value, and visa versa. Accordingly, the output of op amp 404 may experience a brief "dead time" when the output of patch-clamp amplifier 408 is invalid. According to various embodiments, first current source 410 and second current source 412 may be configured to introduce a DC offset that is capable of eliminating the "dead time" that occurs due to the finite slew rate of op amp 404 by introducing an offset that is sufficient to eliminate sign changes or transitions between positive and negative voltages in the output voltage of op amp 404.

For example, if the electrode current $I_{ELEC}$ oscillates between −100 pA to +100 pA, first current source 410 may be configured to introduce a positive DC offset of +200 pA to ensure that the total input current $I_{IN}$ swings between +100 pA and +300 pA. Once the DC offset has been introduced, the input current is always positive and no "dead time" due to transitions occurs. Similarly, second current source 412 may be configured to introduce a negative DC offset to ensure that the input current is always negative and no "dead time" due to transitions occurs. The DC offset may subsequently be subtracted by the computer system or digital controller 414 to restore an accurate value of measured current.

In various embodiments, the DC offset may be added automatically. For example, digital controller 414 may be configured to periodically sample and monitor output voltages generated by op amp 404 and currents calculated based on the measured output voltages. In response to detecting a change in polarity of either the measured voltages or calculated currents, digital controller 414 may configure one or more of first current source 410 and second current source 412 to generate a DC offset sufficient to eliminate the change in polarity. In some embodiments, digital controller 414 may be configured to incrementally add a DC offset in this way until no additional change in polarity is detected in the output of op amp 404. According to various embodiments, digital controller 414 may be configured to generate a notification in response to detecting polarity changes. Thus, a user may be provided with a notification that notifies the user that changes in polarity are occurring.

As similarly discussed above with reference to FIG. 2, current measurement circuit 400 may include feedback capacitance 416. The optimum value for feedback capacitance 414 may vary depending on the input current level. For example, the optimum value may lie in the range of 10 femtofarads and 100 picofarads. To ensure that the optimal value of capacitance is chosen for feedback capacitance 414 at a given time in the operation of current measurement circuit 400, feedback capacitance may be variable, configurable, and programmable, as discussed in greater detail below with reference to FIG. 5.

Figure 5:
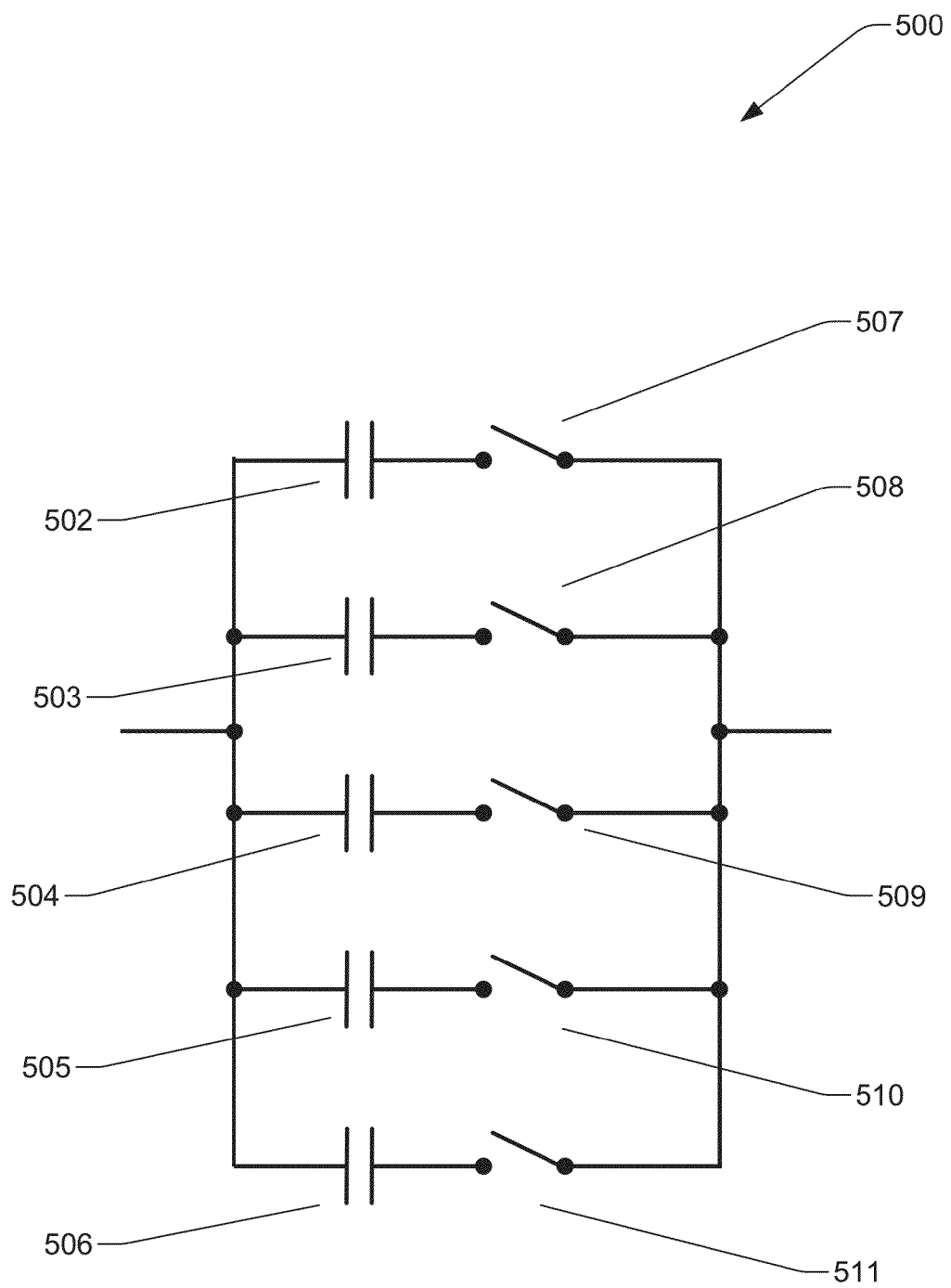
FIG. 5 illustrates an example of a variable and programmable feedback capacitance, in accordance with some embodiments.

FIG. 5 illustrates an example of a variable and programmable feedback capacitance, in accordance with some embodiments. Feedback capacitance 500 may include one or more binary-weighted capacitors, such as capacitors 502-506, and one or more switches, such as MOSFET switches 507-511 that may be configured to couple one or more selected capacitors in parallel. Capacitors 502-506 may have the same or different values. Thus, the configuration of switches 507-511 may modify the total capacitance of feedback capacitance 500 by coupling one or more of capacitors 502-506, which may have different values, in parallel. In some embodiments, the operation of switches 507-511 is controlled by a computer or digital controller. For example, a digital controller may be configured to select or configure feedback capacitance 500 based on the current passing through the electrode. The relationship between the capacitance and the amount of current may be predetermined and previously programmed into the digital controller. Thus, in response to detecting a particular amount of current, the digital controller may look up a capacitance in a previously configured lookup table. The digital controller may then open or close one or more of switches 507-511 to generate a feedback capacitance equal to the capacitance identified in the lookup table based on the electrode current.

Figure 6:
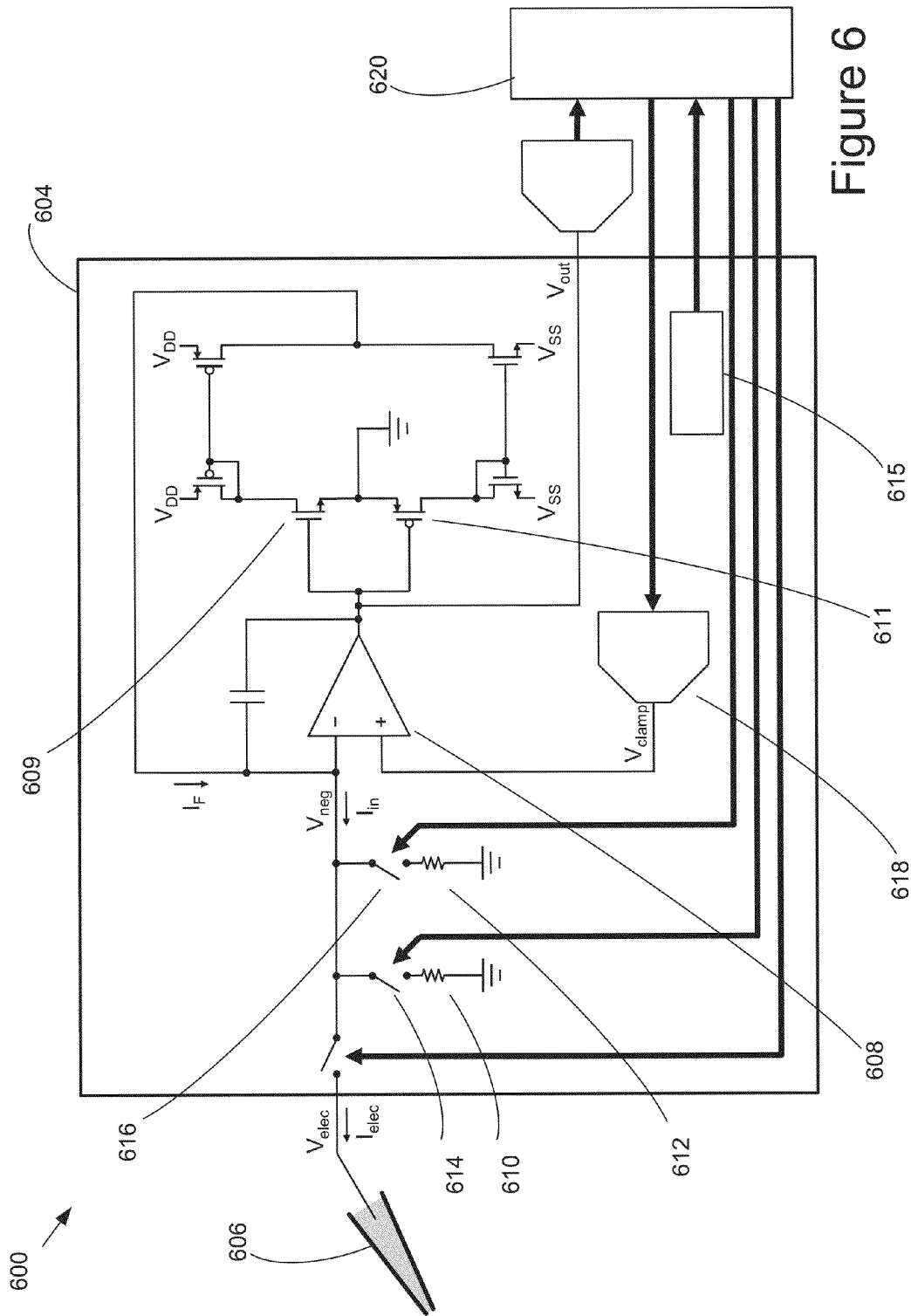
FIG. 6 illustrates an example of a patch-clamp current measurement circuit that may be calibrated by a second calibration circuit, in accordance with some embodiments.

FIG. 6 illustrates an example of a patch-clamp current measurement circuit that may be calibrated by a second calibration circuit, in accordance with some embodiments. The second calibration circuit may include one or more switches, which may be configured to isolate patch-clamp amplifier 604 from electrode 606 during one or more calibration operations associated with patch-clamp amplifier 604. In various embodiments, the second calibration circuit may include one or more resistors coupled to ground and coupled to a negative input of op amp 608 via the one or more switches. In this example, the one or more resistors include resistor 610, $R_{CAL1}$, and resistor 612, $R_{CAL2}$, which are coupled to the negative terminal of op amp 608 via switch 614 and switch 616 respectively. Switch 614 may be set to a first open position or configuration in which resistor 610 is not electrically coupled to op amp 608. Switch 614 may also be set to a first closed position or configuration in which resistor 610 is electrically coupled to op amp 608. Similarly, switch 616 may be set to a second open position or configuration in which resistor 612 is not electrically coupled to op amp 608. Switch 616 may also be set to a second closed position or configuration in which resistor 612 is electrically coupled to op amp 608. Thus, switch 614 and switch 616 may be open or closed to create an equivalent total resistance, $R_{cAE}$ between the negative input of op amp 608 and the circuit ground. By implementing different configurations of the switches, the total resistance may be varied, and the input current may be varied. In some embodiments, digital controller 620 is configured to control the operation of switch 614 and switch 616.

The voltage at the negative input of op amp 608, $V_{NEG}$, is nearly identical to the voltage $V_{CLAMP}$ due to negative feedback. Therefore, the voltage at the negative input terminal may be controlled by setting the $V_{CLAMP}$ controlled by digital-to-analog converter 618. As determined by Ohm's law, the input current, $I_N$, received by patch-clamp amplifier 604 is equal to $V_{NEG}/R_{CAL}$. Therefore, different positive and negative input currents may be generated by varying the magnitudes and values of $V_{CLAMP}$ and/or $R_{CAL}$.

Accordingly, the values of $V_{CLAMP}$ and/or $R_{CAL}$ may be modified to perform a first phase of a calibration process in which a first and second known positive input current are generated to produce a first and second positive output voltage at the output of patch-clamp amplifier 604. Furthermore, the values of $V_{CLAMP}$ and/or $R_{CAL}$ may be modified to perform a second phase of a calibration process in which a first and second known negative input current are generated to produce a first and second negative output voltage. The output voltages may be used to calculate the unknown parameters $I_0$ and $nV_T$ for devices 609 and 611. As previously discussed, additional known currents may be used to obtain additional measurements of output voltages and a more data points that may be used to determine the one or more thermal constants associated with the transistor devices.

In various embodiments, the parameters that are determined during the calibration process are functions of temperature. The thermal voltage $V_T$ is proportional to absolute temperature, but $I_0$ and n also change with temperature in complex ways. Therefore, if the temperature of the chip on which patch-clamp amplifier 604 is implemented changes after calibration, the accuracy of the conversion from output voltage to electrode current will decrease. In some embodiments, the chip or circuit board on which patch-clamp amplifier 604 is implemented may also include a thermal sensor, such as temperature sensor 615, which may be configured to sense one or more thermal metrics associated with transistor devices included in patch-clamp amplifier 604. For example, temperature sensor 615 may periodically measure the temperature of the environment surrounding patch-clamp amplifier 604, and/or may measure the temperature of one or more thermal probes included in patch-clamp amplifier 604. In various embodiments, temperature sensor 615 is located near patch-clamp amplifier 604 on the same chip. If a significant change in temperature is detected after calibration, a new calibration sequence may be triggered or the parameters may be recalculated by the computer based on known or previously measured temperature dependencies, as discussed in greater detail below.

For example, temperature sensor 615 may monitor the temperature of current measurement circuit 600, patch-clamp amplifier 604, and/or various transistor devices included in a feedback circuit of patch-clamp amplifier 604, such as device 609 and device 611. Temperature sensor 615 may take the measurements periodically, and generate a signal or output that is provided to digital controller 620. In various embodiments, digital controller 620 may be configured to monitor the signal or output generated by temperature sensor 615, and may be further configured to initiate one or more calibration operations and/or generate a notification in response to detecting or identifying one or more conditions. For example, digital controller 620 may be configured to record the temperature at which the last calibration occurred, and be further configured to initiate one or more calibration operations and/or generate a notification in response to determining the temperature identified by the output of temperature sensor 615 has deviated more than a predetermined threshold from the last recorded temperature. In some embodiments, digital controller 620 may be configured to include one or more data tables, such as a lookup table that may be used to look up thermal constants based on a measured temperature. In this instance, no additional calibration operations are performed because digital controller 620 looks up the constants in the lookup table instead of recalculating them.

Figure 8:
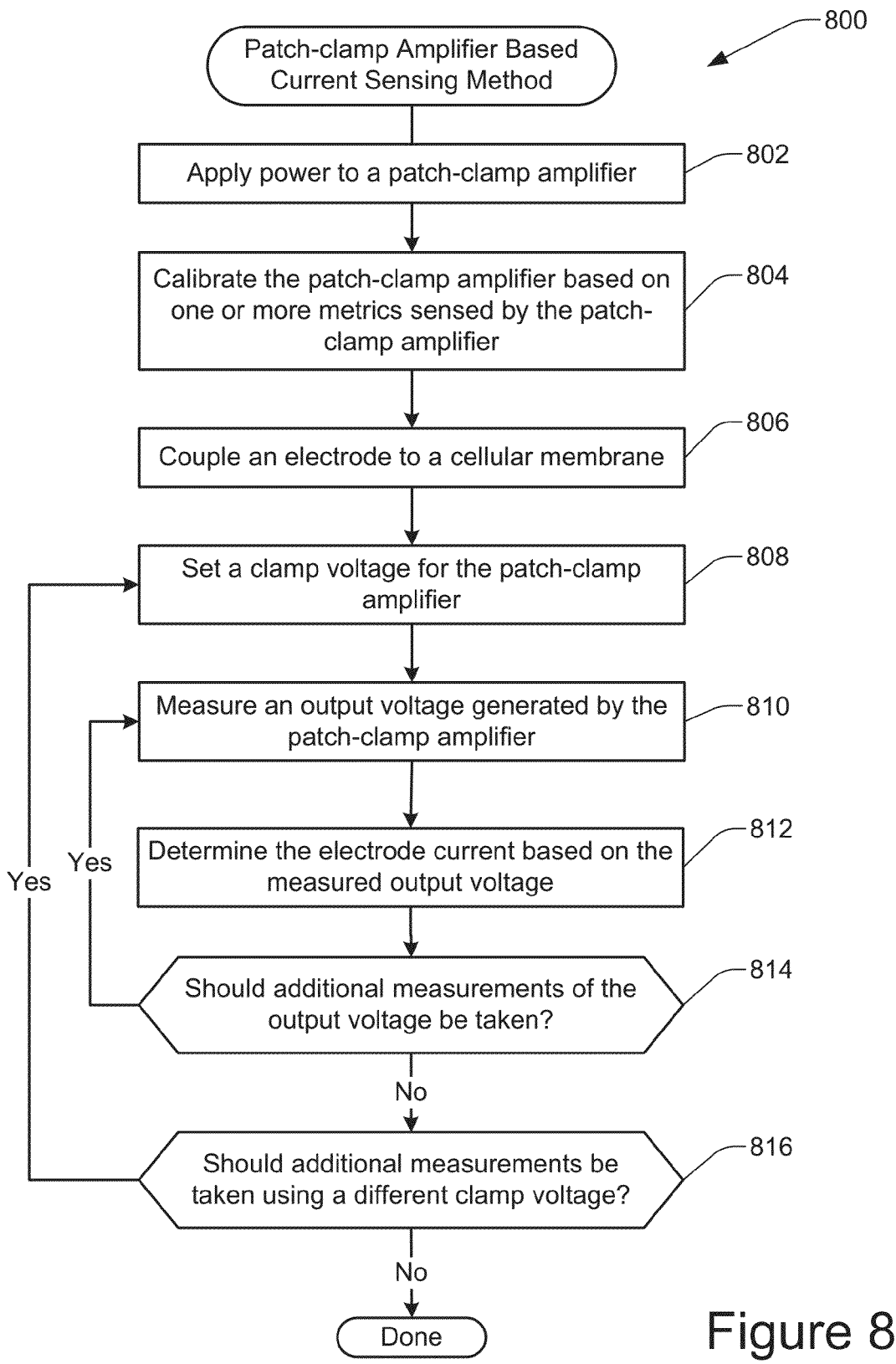
FIG. 8 illustrates an example of a flow chart of a method for using a current-sensing patch-clamp amplifier, in accordance with some embodiments.

FIG. 8 illustrates an example of a flow chart of a method for using a patch-clamp current measurement circuit, in accordance with some embodiments. The patch-clamp amplifier may include transistor-based elements, thus enabling the entire patch-clamp amplifier to be implemented on a microchip. Furthermore, a configuration circuit may also be implemented on the same chip as the patch-clamp amplifier, or included in or integrated with the patch-clamp amplifier itself. The configuration circuit may be configured to initiate and execute one or more calibration operations to ensure that the output of the patch-clamp amplifier is processed and displayed accurately, and is not affected by changes in the operating environment of the circuit elements implemented on the chip. Thus, according to various embodiments, the patch-clamp amplifier may provide calibrated measurements that may be used to reconstruct current changes in a biological environment, such as a biological cell.

Accordingly, at step 802, power may be applied to the patch-clamp amplifier. The power may be applied by a power source, such as a current source or a voltage source, until the chip on which the patch-clamp amplifier is implemented has reached a thermal equilibrium. In some embodiments, the power may be applied to the chip for a previously determined period of time, such as several seconds. According to various embodiments, the circuit implemented on the chip may also include a thermal sensor. The period or amount of time the power is applied may be determined based on one or more metrics sensed by the thermal sensor. For example, a computer or digital controller that monitors and controls operation of the patch-clamp amplifier may monitor sensor readings taken by the thermal sensor, which may be a temperature sensor. The computer or digital controller may initiate application of power to the chip, and periodically measure temperature readings generated by the thermal sensor. Initially, as the circuit initially receives power, the readings may vary greatly between successive measures. As the circuit achieves thermal equilibrium, the readings will vary less. Once the readings vary less than a predetermined amount, such as a threshold value or a rate which may be predetermined or configured by a user, the computer system or digital controller may cease application of the power to the circuit.

At step 804, the patch-clamp amplifier may be calibrated based on one or more sensed metrics. As previously discussed with reference to FIGS. 4 and 5, various different configurations of a patch-clamp amplifier capable of self-calibration are contemplated and disclosed herein. Accordingly, the patch-clamp amplifier implemented on the chip may be calibrated by one or more calibration operations to ensure that the measured output voltages represent the electrode current as accurately as possible. In some embodiments, a calibration circuit implemented on the chip may be used to supply known input currents to the patch-clamp amplifier, which may generate output voltages in response to receiving the known input currents. For example, the calibration circuit may provide the patch-clamp amplifier with two known positive currents and two known negative currents. The resultant output voltages may be measured by an analog-to-digital converter and processed by a computer system. In this way, the measured output voltages and known input currents may be used to calculate the four previously discussed transistor parameters at the transistors' current operating temperatures. Accordingly, the patch-clamp amplifier implemented on the chip may be dynamically calibrated specifically for the thermal equilibrium at which the patch-clamp amplifier is operating.

At step 806, an electrode may be coupled with a biological cell. In some embodiments, manual or automated positioners may be used to contact the cell with the electrode tip. In various embodiments, a gigaohm seal forms between the electrode and the cell as a result of the contact. As previously discussed, once the gigaohm seal has been formed, the patch-clamp amplifier may be capable of measuring voltages and currents associated with electrical activity within the cell.

Accordingly, at step 808, a clamp voltage may be set for the patch-clamp amplifier. As similarly discussed above, the clamp voltage may be a predetermined voltage controlled by a computer system or digital controller and held constant during the operation of the patch-clamp amplifier. In various embodiments, the value of the clamp voltage may be determined by the computer system or digital controller based on a predetermined measurement sequence. For example, a digital controller may be configured or programmed to set the clamp voltage at a predetermined value, continue with method 800 and process one or more measurements as discussed below, and increment the clamp voltage by a predetermined amount. In this way, a series of measurement operations may be performed to complete a measurement sequence.

At step 810, an output voltage generated by the patch-clamp amplifier may be measured. In some embodiments, the measurement may be made by an analog-to-digital converter. Thus, the patch-clamp amplifier may generate an output voltage based on the clamp voltage, the feedback current provided by one or more transistors included in the patch-clamp amplifier, and electrical activity within or associated with the cell attached to the electrode. The resulting output voltage, which may be an analog signal, may be measured and digitized into a digital signal by the analog-to-digital converter. The output of the analog-to-digital converter may be provided to a computer system for further processing.

At step 812, the electrode current may be reconstructed based on the measured output voltage. A computer system or digital controller may receive the output of the analog-to-digital converter and may perform an exponentiation on the digitized output voltage. As similarly discussed above with reference to FIGS. 4 and 5, the transistor parameters calculated at step 804 may be used to convert the exponentiated output voltages to a measured current. Thus, a computer system or digital controller may process measured output voltages to reconstruct the input current which generated the measured output voltages. In this way, the computer system or digital controller may generate a reconstruction of the electrode current, and the corresponding cellular current which the electrode is sensing.

At step 814, it may be determined whether or not additional measurements of the output voltage of the patch-clamp amplifier should be taken. In some embodiments, this determination may be made by the computer system or digital controller based on a previously determined measurement sequence. If it is determined that additional output voltage measurements should be taken, method 800 may return to step 810. In some embodiments, successive measurements taken by iterations of steps 810 through 814 may be performed rapidly. For example, repeated measurements of output voltages may be taken at 10,000 to 50,000 times per second. The measured output voltages taken during the iterations of steps 810 through 814 may provide a plurality of data points that may be used to reconstruct a current waveform that represents the electrode current during the period of time in which the measurements were taken. Thus, the constructed waveform may display how the cellular currents change over time with high accuracy and temporal resolution. If it is determined that additional measurements of the output voltage of the patch-clamp amplifier should not be taken, method 800 may proceed to step 816.

At step 816, it may be determined whether or not additional measurements of output voltages of the patch-clamp amplifier circuit should be taken using a different clamp voltage. In various embodiments, this determination may be made based on a predetermined measurement sequence executed by a computer system or digital controller. If it is determined that additional measurements should be taken at a different clamp voltage, method 800 may return to step 808 and repeat steps 808-814 for the different clamp voltage. If it is determined that no additional measurements should be taken, method 800 may terminate and the current waveform constructed based on the measurements may be provided to a user at a display device of a computer system.

While many of the embodiments disclosed herein have described applications relating to electrodes, such as micropipette electrodes, which may be patched to biological cells, such as neurons, the patch-clamp amplifier circuits described herein may also be used with other types of electrodes in other applications. For example, the patch-clamp amplifier circuits described herein may also be used to perform fast-scan cyclic voltammetry (FSCV), which may be used to detect the presence and concentration of neurotransmitters or other chemical compounds in solution. FSCV often uses carbon-fiber microelectrodes. The clamping voltage $V_{CLAMP}$ may be swept back and forth over a range of approximately −0.6 V to +1.0 V at a scan rate of approximately 300 V/s, and the electrode current may be measured at many intermediate voltages during these excursions. Small variations in the electrode current at particular voltages may provide signatures for various neurotransmitters or other chemical compounds.

While one or more embodiments have been described by way of example and in terms of the specific embodiments, it is to be understood that one or more embodiments are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An apparatus for sensing currents conducted via an electrode, the apparatus comprising:
   an operational amplifier including a first input terminal, a second input terminal, and an output terminal, the first input terminal being configured to electrically couple with the electrode;
   a feedback circuit coupling the output terminal of the operational amplifier to the first input terminal, the feedback circuit comprising a plurality of transistor devices configured to generate a feedback current based on a voltage value of the output terminal, and further configured to provide the feedback current to the first input terminal, wherein the plurality of transistor devices comprises a first set of transistor devices configured to generate a positive feedback current in response to the voltage value of the output terminal being positive, and wherein the plurality of transistor devices further comprises a second set of transistor devices configured to generate a negative feedback current in response to the voltage value of the output terminal being negative; and
   a voltage source coupled to the second input terminal and configured to maintain a substantially constant voltage at the second input terminal.

2. The apparatus of claim 1 further comprising a first calibration circuit, the first calibration circuit comprising:
   a first current source configured to generate a first current in response to receiving a first input from a digital controller; and
   a second current source configured to generate a second current in response to receiving a second input from the digital controller,
   wherein the operational amplifier is configured to generate a first output voltage in response to receiving the first current and is further configured to generate a second output voltage in response to receiving the second current, and
   wherein the digital controller is configured to determine one or more constants associated with the plurality of transistor devices based, at least in part, on the first output voltage and the second output voltage.

3. The apparatus of claim 2, wherein at least one of the first current source or the second current source is configured to provide a direct current (DC) offset to the first input terminal in response to the voltage value of the output terminal changing polarity.

4. The apparatus of claim 1 further comprising a second calibration circuit, the second calibration circuit comprising:
   a first resistive device coupled to a circuit ground;
   a first switch coupling the first input terminal to the first resistive device and having a first open position and a first closed position, wherein the first switch in the first closed position is configured to generate a first current;
   a second resistive device coupled to the circuit ground; and
   a second switch coupling the first input terminal to the second resistive device and having a second open position and a second closed position, wherein the second switch in the second closed position is configured to generate a second current.

5. The apparatus of claim 1 further comprising:
   a thermal sensor configured to sense one or more thermal metrics associated with the plurality of transistor devices, and further configured to generate an output signal identifying the one or more thermal metrics; and
   a digital controller configured to perform one or more calibration operations in response to the thermal sensor generating the output signal.

6. The apparatus of claim 1,
   wherein the first set of transistor devices includes a first transistor device having a first controlling terminal coupled to the output terminal of the operational amplifier, the first transistor device being configured to generate a first feedback current that is an exponential function of the voltage value of the output terminal,
   wherein the first set of transistor devices is configured to generate the positive feedback current by mirroring the first feedback current, and is further configured to provide the positive feedback current to the first input terminal of the operational amplifier,
   wherein the second set of transistor devices includes a second transistor device having a second controlling terminal coupled to the output terminal of the operational amplifier, the second transistor device being configured to generate a second feedback current that is an exponential function of the voltage value of the output terminal, and
   wherein the second set of transistor devices is configured to generate the negative feedback current by mirroring the second feedback current, and is further configured to provide the negative feedback current to the first input terminal of the operational amplifier.

7. The apparatus of claim 6, wherein a first source terminal of the first transistor device is coupled to a circuit ground, and wherein a second source terminal of the second transistor device is coupled to the circuit ground.

8. The apparatus of claim 1, wherein the operational amplifier and the feedback circuit are implemented on a single microchip.

9. A method for sensing currents conducted via an electrode, the method comprising:
- coupling a first input terminal of an operational amplifier to an electrode;
- setting a value of a voltage provided to a second input terminal of the operational amplifier;
- generating, using a plurality of transistor devices, a feedback current and providing the feedback current to the first input terminal and the electrode, the feedback current maintaining a substantially constant voltage at the first input terminal and the electrode, the generating of the feedback current comprising using a first set of transistor devices to generate a positive feedback current in response to an output terminal of the operational amplifier having a positive voltage value, and the generating of the feedback current comprising using a second set of transistor devices to generate a negative feedback current in response to the output terminal of the operational amplifier having a negative voltage value;
- measuring a voltage at the output terminal of the operational amplifier;
- performing, using a computer system, one or more processing operations on the measured voltage; and
- determining a current flowing through the electrode during the measuring step based on a result of the one or more processing operations.

10. The method of claim 9 further comprising performing one or more calibration operations, the one or more calibration operations comprising:
- generating a first current;
- measuring a first voltage at the output terminal of the operational amplifier;
- generating a second current;
- measuring a second voltage at the output terminal of the operational amplifier; and
- determining, using the computer system, one or more constants associated with the plurality of transistor devices based on the measured first voltage and second voltage.

11. The method of claim 10, wherein the one or more calibration operations are performed in response to detecting one or more thermal conditions associated with the plurality of transistor devices.

12. The method of claim 10, wherein the first current is generated by a first current source in response to receiving a first input from a digital controller, and wherein the second current is generated by a second current source in response to receiving a second input from a digital controller.

13. The method of claim 12 further comprising:
- generating a direct current (DC) offset, wherein the DC offset is provided to the first input terminal in response to a voltage value of the output terminal changing polarity, and wherein the DC offset is generated by at least one of the first current source and the second current source.

14. The method of claim 9 further comprising repeating the measuring, performing, and determining steps to generate a plurality of data points.

15. The method of claim 9 further comprising:
- coupling the electrode to a cellular membrane, wherein the coupling generates a seal between the electrode and the cellular membrane.

16. A system for sensing currents conducted via an electrode, the system comprising:
- a patch-clamp amplifier implemented on a chip, the patch-clamp amplifier comprising:
  - an operational amplifier including a first input terminal, a second input terminal, and an output terminal, the first input terminal being configured to electrically couple with the electrode;
  - a feedback circuit coupling the output terminal of the operational amplifier to the first input terminal, the feedback circuit comprising a plurality of transistor devices configured to generate a feedback current based on a voltage value of the output terminal, and further configured to provide the feedback current to the first input terminal;
  - a voltage source coupled to the second input terminal and configured to maintain a substantially constant voltage at the second input terminal;
- an analog-to-digital converter coupled to an output port of the patch-clamp amplifier, the analog-to-digital converter configured to digitize an output generated by the patch-clamp amplifier; and
- a digital controller coupled to the analog-to-digital converter, the digital controller configured to determine a current at the first input terminal based on the digitized output received from the analog-to-digital converter.

17. The system of claim 16, wherein the patch-clamp amplifier further comprises a calibration circuit, the calibration circuit comprising:
- a first current source configured to generate a first current in response to receiving a first input from a digital controller; and
- a second current source configured to generate a second current in response to receiving a second input from the digital controller,
- wherein the operational amplifier is configured to generate a first output voltage in response to receiving the first current and is further configured to generate a second output voltage in response to receiving the second current, and
- wherein the digital controller is configured to determine one or more constants associated with the plurality of transistor devices based, at least in part, on the first output voltage and the second output voltage.

18. The system of claim 16, wherein the patch-clamp amplifier further comprises a calibration circuit that comprises:
- a first resistive device coupled to a circuit ground;
- a first switch coupling the first input terminal to the first resistive device and having a first open and closed position, wherein the first switch in the first closed position is configured to generate a first feedback current;
- a second resistive device coupled to the circuit ground; and
- a second switch coupling the first input terminal to the second resistive device and having a second open and closed position, wherein the second switch in the second closed position is configured to generate a second feedback current.

19. The system of claim 16, wherein the patch-clamp amplifier further comprises:
- a thermal sensor configured to sense one or more thermal metrics associated with the plurality of transistor devices, and further configured to generate an output signal identifying the one or more thermal metrics, and
- wherein the digital controller is configured to perform one or more calibration operations in response to the thermal sensor generating the output signal.

20. The system of claim 16, wherein the patch-clamp amplifier, the analog-to-digital converter, and the digital controller are implemented on a single microchip.

\* \* \* \* \*